(12) United States Patent
Tranchant et al.

(10) Patent No.: US 9,445,974 B2
(45) Date of Patent: Sep. 20, 2016

(54) MASCARA IN POWDER FORM

(75) Inventors: Jean-François R. Tranchant, Marigny les Usages (FR); Emilie J. Gombart, Orleans (FR)

(73) Assignee: LVHM RECHERCHE, Saint Jean de Braye (FR)

(*) Notice: Subject to any disclaimer, the term of this patent is extended or adjusted under 35 U.S.C. 154(b) by 291 days.

(21) Appl. No.: 14/241,040

(22) PCT Filed: Aug. 7, 2012

(86) PCT No.: PCT/FR2012/051857
§ 371 (c)(1),
(2), (4) Date: Jun. 5, 2014

(87) PCT Pub. No.: WO2013/030485
PCT Pub. Date: Mar. 7, 2013

(65) Prior Publication Data
US 2014/0314463 A1    Oct. 23, 2014

(30) Foreign Application Priority Data
Aug. 26, 2011  (FR) ..................... 11 57552

(51) Int. Cl.
*A61K 8/02* (2006.01)
*A61Q 1/10* (2006.01)
(Continued)

(52) U.S. Cl.
CPC ............ *A61K 8/0245* (2013.01); *A45D 33/26* (2013.01); *A45D 40/26* (2013.01); *A61K 8/022* (2013.01); *A61K 8/8111* (2013.01);
(Continued)

(58) Field of Classification Search
CPC ..... A61K 8/0245; A61K 8/8182; A61K 8/86
USPC .............................. 401/1; 424/401, 70.7, 402
See application file for complete search history.

(56) References Cited

U.S. PATENT DOCUMENTS 5,853,010 A    12/1998  Suh
6,009,884 A    1/2000   Suh
(Continued)

FOREIGN PATENT DOCUMENTS

EP    1466580    10/2004
EP    1955610    8/2008
(Continued)

OTHER PUBLICATIONS

Database GMPD [Online] Mintel; Apr. 2002 "Cake Mascara"; XP002674408, Database accession No. 93035, Cake Mascara Longcils Boncza/Ingredients (1 page).

*Primary Examiner* — Jennifer C Chiang
(74) *Attorney, Agent, or Firm* — Hamre, Schumann, Mueller & Larson, P.C.

(57) ABSTRACT

The mascara in powder form comprises at least a first polymer whose melting point is between 35° C. and 70° C., and a second polymer with a melting point of between 80° C. and 150° C. The first polymer may be chosen from vinylpyrrolidone copolymers, and polyalkylene glycols. The second polymer may be chosen from polybutenes, preferably with an average molecular weight of between 300 and 2500 g/mol, and polyvinylpyrrolidones, preferably with an average molecular weight of between 10 000 and 100 000 g/mol. The mascara in powder form is taken up in the desired amount and is then heated before application or at the time of application to the keratin fibers.

22 Claims, 1 Drawing Sheet

(51) Int. Cl.
    *A61K 8/81*    (2006.01)
    *A61K 8/86*    (2006.01)
    *A45D 33/26*   (2006.01)
    *A45D 40/26*   (2006.01)
    *A61Q 1/00*    (2006.01)

(52) U.S. Cl.
    CPC .......... *A61K 8/8176* (2013.01); *A61K 8/8182* (2013.01); *A61K 8/86* (2013.01); *A61Q 1/00* (2013.01); *A61Q 1/10* (2013.01); *A61K 2800/24* (2013.01); *A61K 2800/594* (2013.01); *Y10T 428/2982* (2015.01)

(56) References Cited

U.S. PATENT DOCUMENTS

| 6,220,252 | B1 | 4/2001 | Heintz |
| 7,083,347 | B2 | 8/2006 | Marcotte et al. |
| 2003/0003154 | A1 | 1/2003 | Poterie |
| 2005/0013838 | A1 | 1/2005 | Poterie |
| 2005/0201958 | A1 | 9/2005 | Poterie |
| 2006/0159643 | A1* | 7/2006 | Jacquier ............ A61K 8/25 424/70.7 |
| 2009/0020133 | A1 | 1/2009 | Gueret |
| 2010/0086507 | A1 | 4/2010 | Gueret |
| 2010/0215701 | A1* | 8/2010 | Loyen ............ A61Q 19/00 424/401 |

FOREIGN PATENT DOCUMENTS

| FR | 2824267 | 11/2002 |
| FR | 2853504 | 10/2004 |
| FR | 2892930 | 5/2007 |
| FR | 2903600 | 1/2008 |
| JP | 2000-175725 | 6/2000 |
| JP | 2003-310336 | 11/2003 |

* cited by examiner

MASCARA IN POWDER FORM

The subject of the invention relates to a mascara composition, which must be heated in order to be applied to keratin fibers.

Mascaras are generally in the form of an emulsion paste in which oils and waxes are dispersed in an aqueous phase. Mascaras also exist in the form of a reverse emulsion, in which the water is dispersed in the fatty phase, or alternatively solid cake mascaras obtained by mixing powders in a preheated and melted fatty substance, which mixture is then hot-cast into a dish before cooling. These mascaras, which generally comprise film-forming polymers and pigments, are usually in liquid or paste form and are applied cold to the eyelashes using a brush.

Mascaras which are heated before or during their application to the eyelashes have recently appeared. These compositions, referred to in the present application as "hot-applied mascaras" are usually conditioned in the form of kits comprising a reservoir, an applicator and a heating device. Numerous variants of these kits exist, depending on whether the heating device is located in the reservoir or in the brush. The heating means may also be dissociated from the conditioning of the mascara composition.

The compositions of the prior art are mascaras in the form of a mass that is solid or pasty at room temperature, which are conditioned in reservoirs from which a portion is taken up using a device comprising heating means (see, for example, patent application FR 2 853 504).

The compositions comprise compounds which have a melting point that is suited to such a use and generally comprise a continuous aqueous phase.

Patent application FR 2 903 600 discloses a mascara comprising an aqueous phase and a heat-gelling polymer.

Patent application FR 2 892 930 discloses a composition comprising an aqueous phase and a fatty phase which itself comprises polyorganosiloxanes.

Hot-applied mascaras undergo, on each application to the eyelashes, a heating and cooling cycle after which the composition regains its initial consistency.

Repetition of these cycles resulting from regular use of the mascara, usually daily use, generally brings about an impairment of the properties of the composition when it contains an ingredient that is degraded by heat, or when it is not heat-stable. After a limited number of cycles, the composition becomes more viscous, to the point that it sometimes sets to a solid; the composition may also lose its keratin fiber covering and adhesion properties.

Mascara compositions comprising an aqueous phase, such as mascaras in oil-in-water emulsion form, are particularly sensitive to these repeated heating-cooling cycles. The reason for this is that the gradual evaporation of the water from the mascara as and when portions are taken up, under the influence of the heat released by the heating instrument, may impair its texture and stability.

The object of the invention is to propose a novel form of hot-applied mascara, which overcomes the drawbacks of the hot-applied mascaras of the prior art, whose composition gradually becomes impaired in the course of their use.

The aim of the invention is also to propose a keratin fiber makeup composition which has good cosmetic properties, in particular uniform deposition, satisfactory adhesion, good staying power and easy removal.

The mascara of the invention especially makes it possible to avoid having to subject the composition to a repetition of heating-cooling cycles.

The mascara of the invention has the additional advantage of being able to be taken up easily before the heating step, which makes it possible to adapt the desired amount, for example to modify the effect that the user wishes to obtain. The rest of the composition is thus spared from having to undergo a heating-cooling cycle, which significantly improves the stability of the mascara and the duration of use of the product. The mascara of the invention thus frees the formulator from being limited in his choice of ingredients to compounds whose structure is heat-sensitive.

A first subject of the invention is thus directed towards a mascara intended to be heated in order to be applied to keratin fibers, in particular the eyelashes, which is in the form of a powder.

The term "mascara" defines a makeup composition intended to be applied to keratin fibers. The mascara is more particularly intended for making up or for the cosmetic treatment of keratin fibers, such as human keratin fibers (eyelashes, eyebrows, hair) and false eyelashes.

It may be a makeup base (or "base coat"), a composition to be applied over a base ("top coat"), or a composition for the cosmetic treatment of keratin fibers.

The mascara of the invention is advantageously anhydrous.

The mascara is anhydrous in the sense that water has not been added during its manufacture. Water may nevertheless remain in the mascara in trace amount, especially less than 5% and preferably less than 3% by weight relative to the weight of the composition.

The anhydrous mascara of the invention thus comprises a water content of less than 5% and preferably less than 3% by weight relative to the weight of the composition.

The size of the particles constituting the powder is adapted so as to enable it to be taken up and to charge the heating applicator with a sufficient amount.

Advantageously, the mascara is a powder consisting of particles whose mean diameter is between 1 µm and 10 mm and advantageously between 20 µm and 1 mm. The particle size of the particles is determined via usual methods such as screening or laser particle size analysis.

According to one embodiment, the powder particles comprise only one continuous phase, which may be lipophilic or hydrophilic. In this case, the powder particles are not microcapsules, in the sense that they do not comprise two continuous phases, for example a liquid core in a solid shell. Such microcapsules are especially described in patent application WO 2006/057 438.

The powder particles are preferably solid at room temperature (25° C.), and the mascara preferably has a melting point of between 35 and 70° C., more preferably ranging from 40 to 50° C. and preferably ranging from 40 to 45° C. The melting point of the mascara may be measured by differential thermal analysis and corresponds to the melting point peak temperature.

The powder particles constituting the mascara advantageously contain at least one polymer, which is preferably film-forming. According to a preferred embodiment, the powder particles constituting the mascara advantageously contain at least two polymers, which are preferably film-forming.

In the present invention, the term "film-forming polymer" means a polymer that is capable of forming a continuous film on a support, by itself or in the presence of an adjuvant such as a plasticizer. The support preferably consists of fibers whose shape and sizes are those of keratin fibers.

In the text, the term "polymer" may denote a homopolymer or a copolymer. The term "copolymer" means a polymer comprising at least two different monomers or blocks, which may be of the same chemical family but of different structure.

The polymer that may be used in the mascara of the invention may be of synthetic or natural origin.

Said polymer may be chosen from lipophilic polymers, for instance:

- linear or branched, saturated or unsaturated alkylcelluloses with an alkyl radical comprising up to 8 carbon atoms, especially ethylcellulose and propylcellulose,
- copolymers of a vinyl ester, for instance vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate or allyl dimethylpropionate/vinyl stearate copolymers,
- hydrogenated or non-hydrogenated polyolefins or poly-α-olefins, especially polymers or copolymers formed from alkene monomers comprising from 2 to 20 carbon atoms, in particular polybutenes, polyisobutenes and polydecenes,
- vinylpyrrolidone (VP) copolymers and especially copolymers of vinylpyrrolidone and of alkene advantageously of 2 to 20 carbon atoms, for instance VP/vinyl acetate, VP/ethyl methacrylate, VP/ethyl methacrylate/methacrylic acid, VP/eicosene, VP/hexadecene, VP/triacontene, VP/styrene or VP/acrylic acid/lauryl methacrylate copolymers or butylated polyvinylpyrrolidone (PVP),
- silicone resins, which are generally soluble or swellable in silicone oils, which are crosslinked polyorganosiloxane polymers, such as polymethylsilsesquioxane resins, siloxysilicate resins, trimethylsiloxysilicate resins, or alternatively copolymers of these silicone resins with polydimethylsiloxanes,
- and mixtures thereof.

The polymer may also be chosen from hydrophilic polymers, for instance:

- polyvinyl alcohols,
- polyalkylene glycols such as polyethylene glycols, preferably those that are in solid form at 30° C.,
- proteins, especially proteins of plant origin such as wheat or soybean proteins, and proteins of animal origin such as keratins,
- cellulose-based polymers, especially hydroxyethylcellulose, hydroxypropylcellulose, methylcellulose, ethylhydroxyethylcellulose or carboxymethylcellulose,
- acrylic polymers, especially polyacrylates or polymethacrylates,
- vinyl polymers such as polyvinylpyrrolidones,
- copolymers of vinylpyrrolidone and of vinyl acetate,
- copolymers of vinylpyrrolidone and of caprolactam,
- chitin or chitosan polymers,
- gum arabics, guar gum, karaya gum,
- xanthan derivatives,
- alginates,
- carrageenans,
- glycoaminoglycans,
- hyaluronic acid and derivatives thereof,
- shellac resin,
- and mixtures thereof.

The film-forming polymer is used alone or as a mixture, in variable proportions, so as to adjust the melting point of the mascara powder.

The total amount of film-forming polymer preferably ranges from 1% to 95% of dry weight of said film-forming polymer relative to the total weight of the mascara.

According to a preferred embodiment, the mascara comprises at least one polymer, preferably a film-forming polymer, whose melting point is between 35° C. and 70° C.

According to a variant, the mascara comprises at least a first polymer, preferably a film-forming polymer, whose melting point is between 35° C. and 70° C., and at least a second polymer, preferably a film-forming polymer, whose melting point is between 80° C. and 150° C. According to one embodiment, the two polymers are hydrophilic. According to another embodiment, the two polymers are lipophilic.

The mass proportion between the first polymer and the second polymer is advantageously between 1 and 20, preferably between 3 and 16 and more preferably between 4 and 10.

The total amount of the first polymer and of the second polymer, when it is present, is between 40% and 95% by weight and better still from 70% to 85% by weight relative to the total weight of the mascara.

The first polymer preferably represents from 55% to 80% by weight and more preferably from 60% to 75% by weight, relative to the total weight of the mascara. The second polymer preferably represents from 1% to 20% by weight and more preferably from 5% to 15% by weight relative to the total weight of the mascara.

The first polymer may be advantageously chosen from polyalkylene glycols, preferably with a molecular weight of between 1000 and 3000 g/mol, and copolymers of vinylpyrrolidone and of alkene, preferably with a molecular weight of between 15 000 and 20 000 g/mol.

The second polymer may be advantageously chosen from polyvinylpyrrolidones, preferably with a molecular weight of between 10 000 and 100 000 g/mol and polybutenes, preferably with a molecular weight of between 300 and 2500 g/mol.

According to a first preferred embodiment of the invention, the composition is lipophilic and contains at least two polymers, preferably film-forming polymers, the first polymer being chosen from copolymers of vinylpyrrolidone (VP) and of alkene, preferably from VP/eicosene, VP/hexadecene, VP/triacontene and VP/styrene copolymers, preferably with a molecular weight of between 15 000 and 20 000 g/mol, and the second polymer being chosen from polyolefins, in particular polybutenes preferably with an average molecular weight advantageously between 300 and 2500 g/mol.

According to a second preferred embodiment of the invention, the composition is hydrophilic and contains two polymers, preferably film-forming polymers, the first polymer being chosen from polyalkylene glycols, for example polyethylene glycols preferably with an average molecular weight of between 1000 and 3000 g/mol, and the second polymer being chosen from polyvinylpyrrolidones (PVP), preferably polyvinylpyrrolidones with an average molecular weight of between 10 000 and 100 000 g/mol and advantageously between 40 000 and 70 000 g/mol.

The mascara of the invention may also comprise at least one auxiliary agent that promotes the formation of a film with the film-forming polymer, said agent possibly being chosen from compounds known to those skilled in the art, especially plasticizers and coalescers.

Besides the film-forming polymer, the mascara of the invention comprises an anhydrous continuous fatty phase in which the film-forming polymer is advantageously uniformly dissolved or dispersed. This anhydrous fatty phase is advantageously solid at room temperature (25° C.) and atmospheric pressure (760 mmHg, i.e. 105 Pa). It may comprise at least one wax chosen from natural or synthetic waxes, which are solid at a temperature of about 30° C. The addition of said wax to the composition is intended to thicken the film and to give the mascara a more viscous texture during its application when it has been melted.

Among the waxes that may be used in the context of the invention, mention may be made of:
- "polar" waxes, for instance beeswax, lanolin wax; rice bran wax, carnauba wax, candelilla wax, ouricury wax, Japan wax, berry wax, sumach wax, montan wax, the waxes obtained by hydrogenation of animal or plant oils containing linear or branched fatty chains, such as jojoba oil, sunflower oil, castor oil, coconut oil, lanolin oil, olive oil esterified with stearyl alcohol, or castor oil esterified with cetyl alcohol,
- "apolar" waxes such as microcrystalline waxes, paraffins, ozokerite, polyethylene waxes, silicone waxes and fluoro waxes, and
- mixtures thereof.

Advantageously, the mascara comprises from 1% to 25% by weight and preferably from 5% to 10% by weight of at least one wax relative to the total weight of the mascara composition.

According to a particularly preferred embodiment, the composition is anhydrous, comprising at least one film-forming polymer, more preferably at least two film-forming polymers, and at least one wax, the wax preferably representing less than 15% by weight relative to the weight of the mascara.

The composition according to the invention may also comprise at least one dyestuff, advantageously chosen from pigments, liposoluble dyes and nacres. The particles constituting these dyestuffs preferably have a diameter not exceeding 200 μm and preferably not exceeding a diameter of 150 μm.

The pigments may be white or colored, mineral and/or organic, and coated or uncoated. Among the pigments that may be used in the mascara of the invention, mention may be made of titanium dioxide, optionally surface-treated, zirconium oxide, zinc oxide or cerium oxide, and also iron oxide or chromium oxide, manganese violet, ultramarine blue, chromium hydrate and ferric blue, carbon black, and dyeing lakes, especially barium, strontium, calcium or aluminum lakes.

The nacres may be chosen from white nacreous pigments such as mica coated with titanium or with bismuth oxychloride, colored nacreous pigments such as titanium mica with iron oxides, titanium mica especially with ferric blue or with chromium oxide, titanium mica with an organic pigment of the abovementioned type, and also nacreous pigments based on bismuth oxychloride.

The mascara advantageously comprises from 5% to 30% by weight and preferably from 10% to 25% by weight of dyestuff relative to the total weight of the mascara.

According to a preferred embodiment, use is made of pigments dispersed in a base such as a wax, for example iron oxide particles dispersed in a wax.

The mascara of the invention preferably comprises less than 5% by weight and preferably less than 3% by weight of a compound that is liquid at room temperature, for instance an oil or a volatile solvent such as isododecane, or a cyclomethicone such as cyclopentasiloxane.

The composition of the invention may also comprise any additive usually used in cosmetics, such as a solid filler, antioxidants, preserving agents, fragrances, cosmetic active agents for treating fibers onto which the composition is applied, for instance emollients, moisturizers, vitamins or sunscreens, and mixtures thereof.

A second subject of the invention is directed toward a process for manufacturing the composition according to the invention, comprising:
- a step of hot-mixing of the mascara components, so as to form a liquid phase,
- a step of cooling,
- and then a step for dividing the mass prepared previously so as to obtain a powder formed from solid particles.

The dividing step may be performed by milling the liquid phase that has solidified beforehand on cooling, or alternatively by atomization of the liquid phase, for example using a fluidized air bed, or alternatively via any other process for obtaining solid particles from a heated liquid phase.

It is thus possible to optimize the particle size of the powder particles constituting the mascara of the invention by adapting the formula or by carefully selecting the conditions of the dividing step. The particle size is thus adapted so as to make it possible to obtain both easy and reproducible uptake and also rapid and total melting of the pulverulent composition at the time of heating for the purpose of applying to the keratin fibers.

A third subject of the invention concerns a makeup kit comprising a mascara, as defined previously, conditioned in a reservoir, and also means for taking up, applying and heating said mascara.

The mascara of the invention is conditioned in a non-compacted form, the solid particles thus not being aggregated or bound by any process such as compacting.

The term "loose powder" may thus advantageously be used to qualify this type of pulverulent composition. In this case, the mascara is conditioned by pouring the powder into the reservoir.

The mascara in powder form is advantageously conditioned in a reservoir, for example a bottle, a dish or a jar.

The kit may comprise an assembly in which the conditioning means and the application means for the mascara of the invention are integrally attached. The reservoir may be physically separate from the application device.

The heating means may be separate from the conditioning and application assembly, or integrated therein.

The application to oil may also serve the function of taking up the composition.

According to a first variant, the uptake means is coupled to or integrated into the reservoir.

The reservoir and/or the uptake means may also comprise means for dispensing an amount of mascara powder of the invention, so as to take up only the amount required for application to the keratin fibers. These dispensing means may advantageously keep the mass of powder hermetically in the reservoir, so as to protect it from moisture or temperature.

According to a second variant, the uptake means is coupled to or integrated into the mascara application means.

According to a third variant, the uptake means is physically separate from the reservoir and the application means.

The heating means is advantageously in the form of a heating device of the type described in U.S. Pat. No. 6,009,884, U.S. Pat. No. 5,853,010 or U.S. Pat. No. 6,220,252. The heating device advantageously comprises elements, for instance a switch for switching the device on or off, a pilot light, the lighting or color change of which indicates that the device is at the temperature required for taking up the powder, and especially at a temperature sufficient to bring about melting of the composition.

The heating device is advantageously coupled to or integrated into the uptake means and/or the application means, which application means then comprises a handling means inside which is located a battery connected to a heating wire, advantageously made of a nickel/chromium alloy, which is itself connected to a resistance which heats the mascara powder taken up.

It is preferred for the application means to integrate a heating means. A heating applicator that may be used for the invention is described, for example, in patent applications JP 2000-175725 and JP 2003-310336. Such a heating applicator is sold in Japan by the company Matsushita under the brand name National® (model EH232).

According to a preferred embodiment, the heating device is arranged so as not to substantially heat all or part of the handling means.

The amount of mascara taken up is placed in contact with the hot part of the handling means and/or of the application means.

Advantageously, the mascara of the invention is heated by the heating device before or during the application of the product by the user to the keratin fibers, for example the eyelashes.

It is also possible to envisage a recharge in the form of a reservoir in which the mascara of the invention is conditioned.

A fourth subject of the invention is directed toward a process for making up or for the cosmetic treatment of keratin fibers, said process comprising a first step of taking up the mascara powder of the invention, followed by a step of heating prior to or concomitant with the application of said mascara, the heating step being directed toward bringing the mascara particles beyond their melting point, and finally a step of applying the heated composition to the keratin fibers, so as to obtain a film producing a makeup effect and/or cosmetic treatment on said fibers.

The invention is in particular directed toward a process for making up or for the cosmetic care of keratin fibers, especially the eyelashes, in which the mascara powder of the invention is heated to a temperature of greater than or equal to 35° C. and less than or equal to 70° C.

The process especially comprises the following steps:
taking up the mascara powder according to the invention, in an amount necessary to make at least one application,
heating the amount of powder taken up to a temperature sufficient to obtain melting of the powder particles,
applying the mascara thus heated to the keratin fibers so as to produce the desired effect.

The invention is illustrated by the examples that follow. In these examples, the percentages are given on a mass basis. The names of the ingredients correspond to their INCI name.

Example 1

Powder Mascara

The mascara having the composition below was prepared according to the process described below.
75% PEG-32 (Pluracare® E1500 supplied by the company BASF, molecular weight 1400-1600 g/mol)
5% Polyvinylpyrrolidone (PVP K30® 100% solid supplied by the company ISP, molecular weight 60 000 g/mol)
20% black iron oxides All the starting materials of formula except for the pigments were heated to a temperature of 80° C.

After mixing by stirring at 1500 rpm using a suitable mixer, the pigments were added and the resulting mixture was then allowed to cool with continued stirring.

The mass obtained after cooling was then milled in an Alpine brand knife mill or pin mill, so as to reduce and homogenize the size of the mascara particles.

Figure 1:
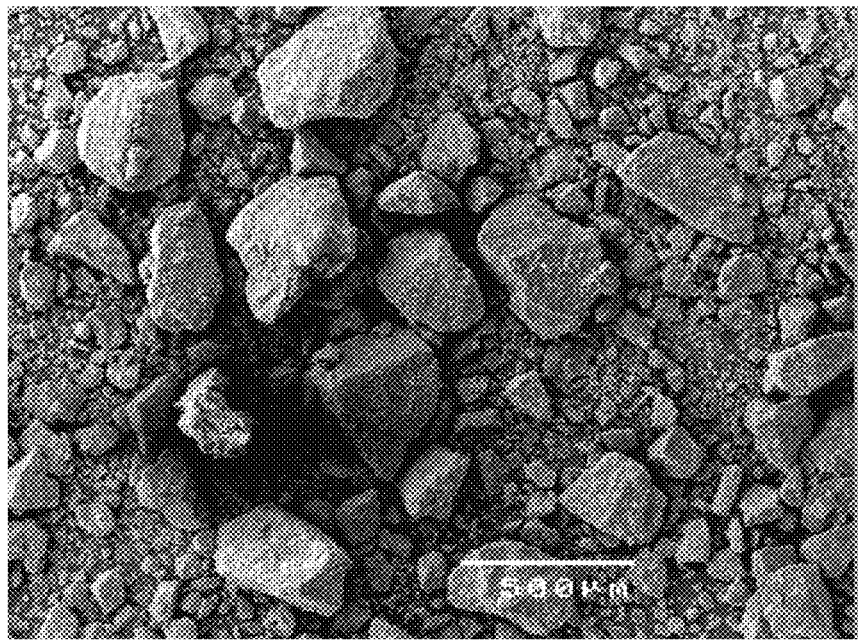
FIG. 1 is an electron microscopy photograph of a representative fraction of the powder according to example 1, obtained after milling.

The particle size of the powder obtained (FIG. 1) consists of a population of particles including a fraction with a particle size of a few hundred microns and a fraction of fine particles whose size is of an order of magnitude ranging from a micron to a few tens of microns.

Measurement of the Melting Point of the Mascara

The melting point of the mascara is measured using a Star SW 9.30 model differential scanning calorimeter (D.S.C.) from the company Mettler. A sample of 12 mg of product placed in a crucible is subjected to a first temperature rise ranging from −50° C. to 100° C., at a heating rate of 10° C./minute, left at the temperature of 100° C. for 1 minute, and then cooled from 100° C. to −50° C. at a cooling rate of 5° C./minute, left at the temperature of −50° C. for 4 minutes, and finally subjected to a second temperature rise ranging from −50° C. to 100° C., at a heating rate of 10° C./minute. During the second temperature rise, the variation of the difference in heat absorbed by the empty crucible and by the crucible containing the sample was measured as a function of the temperature. The melting point of the mascara is the temperature value corresponding to the top of the peak of the curve representing the variation of the difference in heat absorbed as a function of the temperature.

The melting point of the mascara measured under these conditions was equal to 50° C.

Example 2

Powder Mascara

Figure 2:
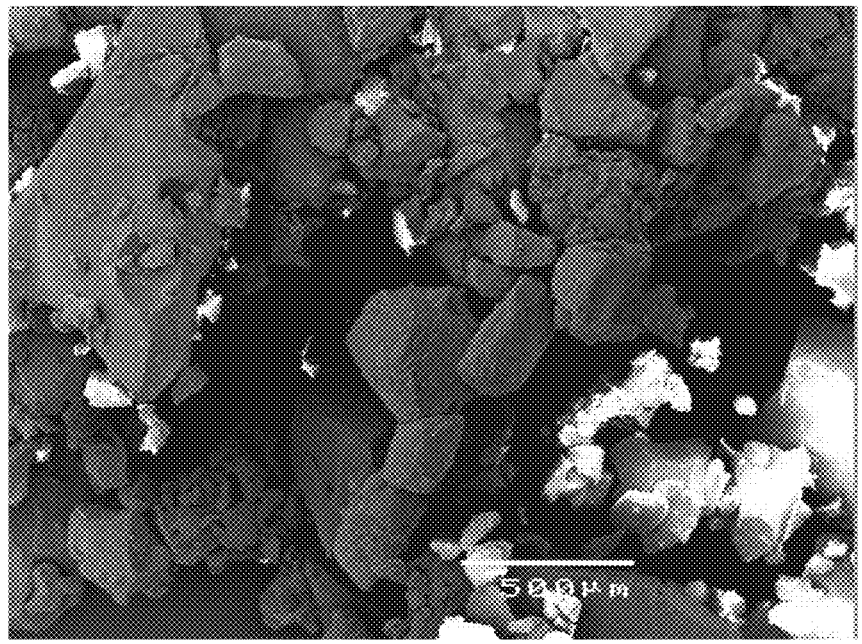
FIG. 2 is an electron microscopy photograph of a representative fraction of the powder according to example 2, obtained after milling.

The mascara having the composition below was prepared according to the same process as that described in example 1.
70% VP/eicosene copolymer (Ganex® 220VF supplied by the company ISP, molecular weight 17 000 g/mol)
10% polybutene (average molecular weight 2000 g/mol)
20% black iron oxides The particle size of the powder obtained (FIG. 2) consists of a population of particles whose particle size is greater than that obtained in example 1, ranging for the present example from a few tens of microns up to a millimeter.

Under the same milling conditions, the disparity of the particle sizes shows that the formula, especially the polymer composition, has an influence on the behavior of the powder with respect to this step.

The melting point of the mascara measured under the same conditions as those of example 1 was equal to 44.8° C.

Example 3

Powder Mascara

The mascara having the composition below was prepared according to the same process as that described in example 1.
65% VP/eicosene copolymer (Ganex® 220VF supplied by the company ISP, molecular weight 17 000 g/mol)
15% polybutene (average molecular weight 2000 g/mol)
20% dispersion of pigments in a wax*
*Dispersion of black iron oxide particles in a wax (INCI= Hydrogenated Vegetable Oil) at a 50/50 w/w ratio.

The melting point of the mascara measured under the same conditions as those of example 1 was equal to 41.1° C.

The invention claimed is:

1. A mascara useful for being heated in order to be applied on keratin fibers, in particular the eyelashes, wherein said mascara is in the form of a powder consisting of particles having a mean diameter between 1 μm and 10 mm, and wherein said mascara comprises at least a first polymer, which is a film-forming polymer and whose melting point is between 35° C. and 70° C.

2. The mascara of claim 1, wherein the powder consists of particles having a mean diameter between 20 μm and 1 mm.

3. The mascara of claim 1, wherein said mascara has a melting point of between 35 and 70° C.

4. The mascara of claim 1, wherein said mascara has a melting point ranging from 40 to 50° C.

5. The mascara of claim 1, wherein said mascara is anhydrous.

6. The mascara of claim 1, wherein said mascara comprises a second polymer, which is a film-forming polymer and whose melting point is between 80° C. and 150° C.

7. The mascara of claim 6, wherein the mass ratio between the first polymer and the second polymer is between 1 and 20.

8. The mascara of claim 6, wherein the mass ratio between the first polymer and the second polymer is between 3 and 16.

9. The mascara of claim 6, wherein the total amount of the first polymer and of the second polymer is from 40% and 95% by weight relative to the total weight of the mascara.

10. The mascara of claim 6, wherein the total amount of the first polymer and of the second polymer is from 70% to 85% by weight relative to the total weight of the mascara.

11. The mascara of claim 6, wherein the first polymer is selected in the group consisting of copolymers of vinylpyrrolidone (VP) and alkene, and the second polymer is chosen from polybutenes.

12. The mascara of claim 6, wherein the first polymer is selected in the group consisting of VP/eicosene, VP/hexadecene, VP/triacontene and VP/styrene copolymers, and the second polymer is chosen from polybutenes having an average molecular weight of between 300 and 2500 g/mol.

13. The mascara of claim 6, wherein the first polymer is a polyethylene glycol, and the second polymer is a polyvinylpyrrolidone.

14. The mascara of claim 6, wherein the first polymer is a polyethylene glycol, and the second polymer is a polyvinylpyrrolidone.

15. The mascara of claim 6, wherein the first polymer is a polyethylene glycol with an average molecular weight of between 1000 and 3000 g/mol, and the second polymer is a polyvinylpyrrolidone with an average molecular weight of between 10 000 and 100 000 g/mol.

16. The mascara of claim 1, wherein said mascara comprises from 1% to 25% by weight of at least a wax, relative to the total weight of the mascara.

17. The mascara of claim 1, wherein said mascara comprises from 5% to 10% by weight of at least one wax relative to the total weight of the mascara.

18. The mascara of claim 1, wherein said mascara comprises from 5% to 30% by weight of dyestuff relative to the total weight of the mascara.

19. The mascara of claim 1, wherein said mascara comprises from 10% to 25% by weight of dyestuff relative to the total weight of the mascara.

20. The mascara of claim 1, wherein said mascara comprises less than 5% by weight of a compound that is liquid at room temperature, chosen in the group consisting of oils and volatile solvents.

21. A makeup kit comprising
a mascara of claim 1 that is held in a reservoir, and
a heater capable of heating said mascara at a temperature of between 35 and 70° C.

22. The makeup kit of claim 21, wherein the heater is coupled to an applicator.

* * * * *